US005723321A

United States Patent [19]

Furui et al.

[11] Patent Number: 5,723,321
[45] Date of Patent: Mar. 3, 1998

[54] PROCESS FOR PREPARING D-LYSINE

[75] Inventors: Masakatsu Furui; Eiji Takahashi, both of Osaka; Hiroyasu Seko, Nara, all of Japan

[73] Assignee: Tanabe Seiyaku Co., Ltd., Osaka, Japan

[21] Appl. No.: 576,566

[22] Filed: Dec. 21, 1995

[30] Foreign Application Priority Data

Dec. 26, 1994 [JP] Japan .................................. 6-322941

[51] Int. Cl.$^6$ .............................. C12P 13/08; C12N 1/20
[52] U.S. Cl. .................. 435/115; 435/252.1; 435/252.2; 435/252.3; 435/253.6; 435/254.1; 435/254.22; 435/254.3; 435/255.7
[58] Field of Search ....................... 435/115, 252.1, 435/252.2, 252.3, 252.33, 252.34, 253.6, 254.1, 254.22, 254.3, 254.5, 255.7, 848, 850, 859, 874, 913

[56] References Cited

U.S. PATENT DOCUMENTS 3,527,776  9/1970  Uzuki ....................................... 260/372

FOREIGN PATENT DOCUMENTS

WO92/10579  6/1992  WIPO .

OTHER PUBLICATIONS

Patent Abstracts of Japan, unexamined applications, C field, vol. 9, No. 78, Apr. 6, 1985, The Patent Office Japanese Government, p. 27 C 274; JP-A-59 210894 (Ajinomoto).

Primary Examiner—David M. Naff
Assistant Examiner—Deborah Ware
Attorney, Agent, or Firm—Finnegan, Henderson, Farabow, Garrett & Dunner, L.L.P.

[57] ABSTRACT

A process for preparing D-lysine using a microorganism which has the ability to asymmetrically degrade L-lysine in a reaction medium is disclosed. The process is performed by first bringing racemic lysine into contact with a culture or a treated culture of the microorganism, and then collecting and isolating the D-lysine from the reaction mixture.

12 Claims, No Drawings

PROCESS FOR PREPARING D-LYSINE

BACKGROUND OF THE INVENTION

This invention relates to a novel process for preparing D-lysine by using a microorganism.

D-Lysine is a useful compound as a starting material or synthetic intermediate for the preparation of various medicines, and an optical resolving agent. In the prior art, as a process for preparing D-lysine, there have been known physicochemical methods such as an optical resolution method by fractional crystallization and chromatography of a racemic compound, or an asymmetric synthetic method in organic chemistry. Further, as a biochemical method, there have been known a method of asymmetrically hydrolyzing 5-(4-aminobutyl)hydantoin by using a microorganism enzyme, a method of hydrolyzing α-amino-ε-caprolactam and a method of hydrolyzing D-N-carbamoyl-α-amino acid (PCT Patent Publication No. WO 92/10579).

However, the above physicochemical methods have disadvantages that operation is complicated or yield and optical purity of a resulting product are low. The biochemical methods have disadvantages that 5-(4-aminobutyl) hydantoin or α-amino-ε-caprolactam which is a substrate is expensive.

SUMMARY OF THE INVENTION

An object of the present invention is to provide a process for preparing D-lysine industrially and advantageously.

The present inventors have studied intensively and consequently found microorganisms having ability of selectively degrading only a L-isomer in a racemic lysine, to accomplish the present invention.

That is, the present invention is a process for preparing D-lysine, which comprises the steps of:

making a culture or treated culture of a microorganism having ability of asymmetrically degrading L-lysine act on a racemic lysine; and separating and collecting remaining D-lysine.

DESCRIPTION OF THE PREFERRED EMBODIMENTS

In the following, the present invention is explained in detail.

The racemic lysine to be used as a starting compound in the present invention may be not only one containing equal amounts of D-isomer and L-isomer, but one containing both of these optical isomers in any ratio of mixture.

The microorganism to be used in the present invention may be any microorganism having ability of asymmetrically degrading L-lysine, i.e., ability of selectively degrading a L-isomer in a racemic lysine. As such a microorganism, there may be mentioned, for example, microorganisms belonging to *Achromobacter, Escherichia, Pseudomonas, Comamonas, Agrobacterium, Proteus, Micrococcus, Flavobacterium, Hafnia* or *Providencia* as bacteria; microorganisms belonging to *Yarrowia, Candida* or *Apiotrichum* as yeasts; or microorganisms belonging to *Penicillium* as molds.

Specific examples of these microorganisms include *Achromobacter delmarvae* IAM 1457 (FERM BP-5290), *Escherichia coli* ATCC 11303, *Escherichia coli* ATCC 11105, *Pseudomonas aureofaciens* IAM 1001, *Pseudomonas fragi* IAM 1650, *Pseudomonas pavonacea* IAM 1155, *Pseudomonas sp.* ATCC 14676, *Pseudomonas putida* ATCC 12633, *Comamonas testosteroni* IAM 1048, *Agrobacterium tumefaciens* No. 417 (FERM BP-5291), *Proteus vulgaris* RIMD KS (IAM 12003), *Micrococcus sp.* IAM 1012, *Flavobacterium rigense* No. 35 (FERM BP-5289), *Hafnia alvei* IFO 3731, *Providencia rettgeri* IFO 13501, *Yarrowia lipolytica* IFO 0717, *Yarrowia lipolytica* IFO 1548, *Yarrowia lipolytica* IFO 0746, *Yarrowia lipolytica* IF0 1195, *Yarrowia lipolytica* IFO 1209, *Candida maltosa* IAM 12247, *Apiotrichum humicola* ATCC 36992, *Penicillium chrysogenum* AHU 8118, *Penicillium citreo-roseum* AHU 8121, *Penicillium citreo-viride* AHU 8123, *Penicillium notatum* AHU 8350 or *Penicillium purpurrescens* AHU 8351.

Among them, preferred are microorganisms belonging to *Pseudomonas, Comamonas, Yarrowia, Achromobacter* or *Agrobacterium*, and particularly preferred are microorganisms belonging to *Pseudomonas* (e.g., *Pseudomonas aureofaciens, Pseudomonas fragi, Pseudomonas pavonacea* or *Pseudomonas putida*) , *Comamonas* (e.g., *Comamonas testosteroni*) or *Yarrowia* (e.g., *Yarrowia lipolytica*).

Three of the microorganisms listed above are on deposit at the National Institute of Bioscience and Human Technology of the Agency of Industrial Science and Technology, the Ministry of International Trade and Industry in Japan. *Flavobacterium rigense* No. 35 (FERM BP-5289) was deposited on May 1, 1981. *Achromobacter delmarvae* IAM 1457 (FERM BP-5290) was deposited on Nov. 14, 1994. *Agrobacterium tumefaciens* No. 417 (FERM BP-5291) was deposited on Dec. 16, 1994.

The microorganism to be used in the present invention may be a strain which is newly separated from soil, food, an animal or the like. Further, there may be used a mutant obtained by artificial treatment such as irradiation of UV ray or treatment using a mutating agent or a strain derived from the above microorganism by a genetic engineering or bioengineering means such as recombination of DNA or cell fusion.

The culture or treated culture of the microorganism to be used in the present invention is any culture or treated culture so long as it has ability of asymmetrically degrading L-lysine. As the culture, there may be mentioned, for example, a culture solution or a living cell, and as the treated culture, there may be mentioned, for example, a washed cell, a dried cell, a culture supernatant, a ground cell, an autolysate of a cell, an extract of a cell, or a partially purified or purified enzyme obtained therefrom according to the conventional manner.

In the present invention, culture of the microorganism may be carried out by, for example, culturing said microorganism in a medium generally used in this field of the art, for example, a conventionally used medium having its source in carbon, nitrogen and containing an inorganic salt, at about pH 5 to 8 at ordinary temperature to under heating (preferably about 20° to 40° C.) and under aerobic conditions. Further, during culture, by adding about 0.001% or more, particularly about 0.1 to 1% of the racemic lysine to the medium, enzyme activity can be heightened.

The living cell and the culture supernatant can be obtained from a culture solution obtained by culturing the microorganism as described above, by operation such as centrifugation or filtration. The washed cell can be obtained by washing a living cell with a physiological saline, and the dried cell can be obtained by subjecting a living cell or a washed cell to lyophilization or acetone drying. The ground cell can be obtained by treating a living cell or a washed cell by various physicochemical methods, for example, ultrasonication, French press, osmotic pressure, freezing and thawing, alumina grinding, lysokinase, a surfactant or an organic solvent. The extract of a cell can be obtained by, for example, removing solids from a ground cell by filtration or centrifugation. The partially purified or purified enzyme can be obtained by, for example, fractionating an enzyme from a fraction of a pulverized cell or a culture supernatant according to a conventional manner such as fractionation using ammonium sulfate, ion exchange chromatography or gel filtration chromatography and purifying the enzyme by using ability of selectively degrading L-lysine as an index.

The above microorganism or treated microorganism may be used as such and may be used after immobilizing it by a polyacrylamide method, a sulfur-containing polysaccharide gel method (e.g., a carrageenan gel method), an alginic acid gel method or an agar gel method.

The asymmetric degradation according to the present invention can be carried out by bringing the racemic lysine which is a starting compound into contact with the microorganism or treated microorganism having ability of asymmetrically degrading L-lysine in a solution, followed by incubation. Further, if desired, the reaction may be carried out concurrently with culturing the microorganism.

The reaction can be carried out suitably in an aqueous solution. Further, the reaction proceeds suitably at ordinary temperature to under heating, preferably 10° to 50° C., particularly preferably 25° to 40° C. It is preferred to adjust the pH of the reaction mixture to 5 to 10, particularly 6 to 9.

The charged concentration (w/v) of the racemic lysine which is a starting compound to be used as a reaction substrate is generally preferably 0.05 to 20%, particularly 0.5 to 10%. The starting compound may be added at one time in the beginning or may be added several times with divided amounts during the reaction.

When the living cell is used in the present invention, it is preferred to add a surfactant to the reaction mixture since the reaction time can be shortened. As an example of the surfactant to be used for the above purpose, there may be mentioned cetyl pyridinium bromide, cetyl trimethylammonium bromide and p-isooctylphenyl ether (Triton X-100, trade name, produced by Rohm & Haas Co., U.S.A.), and it is preferred to use the surfactant in an amount of about 0.0001 to 0.1% based on the amount of the reaction mixture.

When the reaction is carried out concurrently with culturing the microorganism, the reaction may be carried out by using a medium to which the racemic lysine is previously added, under the same conditions as those of culture.

After completion of the reaction, collection and isolation of D-lysine from the reaction mixture can be carried out easily according to the conventional manner. For example, after insoluble materials such as a cell are removed from the reaction mixture by centrifugation, the reaction mixture is placed in an ion exchange resin to make a product to be adsorbed into the resin. The product is eluted with aqueous ammonia and concentrated under reduced pressure. Thereafter, the pH of the reaction mixture is adjusted to 6.0, and the reaction mixture is subjected to crystallization from ethanol to obtain crystals of D-lysine monohydro-chloride.

Detection whether or not the microorganism or treated microorganism has ability of asymmetrically degrading L-lysine can be carried out easily according to the above reaction method, for example, as described below. That is, the microorganism or treated microorganism to be detected is added to a medium or aqueous solution containing the racemic lysine, and the mixture is shaken at 30° C. for 120 hours. The solution after completion of the reaction is analyzed and quantitated by high performance liquid chromatography using an optically active column (e.g., CROWNPAK CR(+), trade name, manufactured by Daicel Kagaku Kogyo Co.) to measure the respective contents of D-lysine and L-lysine. By the measurement, for example, when it is found that a L-isomer is reduced and a D-isomer remains in the racemic lysine, it is judged that the microorganism or treated microorganism has ability of asymmetrically degrading L-lysine.

EXAMPLES

The present invention is described in detail by referring to Examples.

In the present specification, "%" always means "weight/volume (g/dl)" Further, in Examples, quantitation of an optical isomer of lysine was carried out by high performance liquid chromatography using CROWNPAK CR(+) (trade name, manufactured by Daicel Kagaku Kogyo Co.).

Example 1

Into a shaking flask having a volume of 500 ml was charged 100 ml of a medium (pH 7.0) comprising 2% of DL-lysine monohydrochloride, 0.2% of ammonium sulfate, 0.1% of potassium dihydrogen phosphate, 0.05% of magnesium sulfate and 0.02% of a yeast extract, and the medium was sterilized at 120° C. for 10 minutes. A loopful of *Yarrowia lipolytica* IFO 1209 was inoculated into the medium, and cultured at 30° C. for 168 hours with shaking. The cell was removed by centrifuging 1000 ml of the above culture broth to obtain a supernatant. After the supernatant was adjusted to have pH 6.0 with hydrochloric acid, ultrafiltration was carried out in order to remove protein and others, whereby a filtrate was obtained. After activated carbon was added to the filtrate to effect decolorization, the filtrate was concentrated under reduced pressure, and 200 ml of ethanol was added to 20 g of the concentrate to obtain 5.8 g of D-lysine monohydrochloride as crude crystals. 5.8 ml of water was added to the crude crystals, and the crude crystals were dissolved by heating, and then recrystallized by cooling to obtain 2.9 g of crystals of D-lysine monohydrochloride.

Optical rotation: $[\alpha]_D^{20}$: −20.9° (C=8, 6N HCl)

Optical purity: 100%

Example 2

Into 100 ml of the medium shown in Example 1 were inoculated microorganisms in Table 1 shown below, respectively. After the microorganisms were cultured while shaking at 30° C. for 120 hours, D-lysine remaining in the culture solution was quantitated. The contents of D-lysine were as shown in Table 1. Further, almost no L-lysine which was an antipode was detected from the culture broth.

TABLE 1

| Name of strain | Remaining D-lysine (mg) |
|---|---|
| *Escherichia coli* ATCC 11303 | 899 |
| *Escherichia coli* ATCC 11105 | 942 |
| *Hafnia alvei* IFO 3731 | 831 |
| *Pseudomonas fragi* IAM 1650 | 896 |
| *Flavobacterium rigense* No. 35 (FERM BP-5289) | 1000 |
| *Pseudomonas putida* ATCC 12633 | 78 |
| *Proteus vulgaris* RIMD KS (IAM | 682 |

TABLE 1-continued

| Name of strain | Remaining D-lysine (mg) |
|---|---|
| 12003) | |
| *Micrococcus sp.* IAM 1012 | 194 |
| *Providencia rettgeri* IFO 13501 | 180 |
| *Yarrowia lipolytica* IFO 0717 | 1000 |
| *Yarrowia lipolytica* IFO 1548 | 1000 |
| *Yarrowia lipolytica* IFO 1195 | 925 |
| *Candida maltosa* IAM 12247 | 1000 |
| *Penicillium chrysogenum* AHU 8118 | 1000 |
| *Penicillium citreo-roseum* AHU 8121 | 953 |
| *Penicillium citreo-viride* AHU 8123 | 1000 |
| *Penicillium notatum* AHU 8350 | 678 |
| *Penicillium purpurrescens* AHU 8351 | 818 |

Example 3

Into a shaking flask having a volume of 500 ml was charged ml of a medium (pH 7.0) comprising 0.5% of DL-lysine monohydrochloride, 1.0% of polypeptone, 1.0% of a yeast extract and 0.5% of sodium chloride, and the medium was sterilized at 120° C. for 10 minutes. A loopful of *Pseudomonas sp.* ATCC 14676 was inoculated into the medium and cultured at 30° C. for 20 hours. The cell collected from 1000 ml of the above culture broth by centrifugation was suspended in a physiological saline and then collected by centrifugation. To the cell was added 500 ml of a 50 mM phosphate buffer (pH 7.0) containing 50 g of DL-lysine monohydrochloride, and the mixture was reacted at 30° C. for 72 hours to degrade L-lysine completely. After the reaction, the cells were removed by centrifugation, and subsequent procedures were carried out in the same manner as in Example 1 to obtain 14.2 g of D-lysine monohydrochloride.

Optical rotation: $[\alpha]_D^{20}$: $-19.5°$ (C=8, 6N HCl)

Optical purity: 100%

Example 4

A loopful of *Comamonas testosteroni* IAM 1048 was inoculated into the medium shown in Example 3 and cultured at 30° C. for 20 hours. By using 1,000 ml of the above culture broth, reaction was carried out in the same manner as in Example 3. After the reaction, the cell was removed by centrifugation to obtain a supernatant. Ultrafiltration was carried out in order to remove protein and others in the supernatant, whereby a filtrate was obtained. The filtrate was placed in an ion exchange resin Diaion SK116 (trade name, produced by Mitsubishi Chemical Corporation) to make the product to be adsorbed into the resin. The product was eluted with aqueous ammonia to obtain an eluate. Further, the eluate was concentrated under reduced pressure, adjusted pH to 6.0 with hydrochloric acid and then subjected to crystallization from ethanol to obtain 17.6 g of crystals of D-lysine monohydrochloride.

Optical rotation: $[\alpha]_D^{20}$:$-20.8°$ (C=8, 6N HCl)

Optical purity: 100%

Example 5

Into the medium shown in Example 3 were inoculated microorganisms in Table 2 shown below, respectively and the microorganisms were cultured at 30° C. for 20 hours. The cells collected from 100 ml of the above culture broth by centrifugation were suspended in a physiological saline and then collected by centrifugation. To the cells was added 50 ml of a 50 mM phosphate buffer (pH 7.0) containing 2.5 g of DL-lysine monohydrochloride, and the mixtures were reacted at 30° C. for 72 hours. The contents of D-lysine of the reaction mixtures were as shown in Table 2. Further, almost no L-lysine which was an antipode was detected from the reaction mixtures.

TABLE 2

| Name of strain | Remaining D-lysine (mg) |
|---|---|
| *Achromobacter delmarvae* IAM 1457 (FERM BP-5290) | 1.1 |
| *Pseudomonas aureofaciens* IAM 1001 | 1.1 |
| *Pseudomonas pavonacea* IAM 1155 | 1.2 |
| *Agrobacterium tumefaciens* No. 417 (FERM BP-5291) | 1.2 |
| *Yarrowia lipolytica* IFO 0717 | 1.1 |
| *Yarrowia lipolytica* IFO 0746 | 1.1 |
| *Apiotrichum humicola* ATCC 36992 | 1.2 |

As described above, according to the process of the present invention, D-lysine can be prepared industrially from an inexpensive racemic lysine with extremely good efficiency, and by selecting enzymatic reaction conditions such as a microorganism suitably, a product having an optical purity of 100% can be obtained. Thus, the process of the present invention is an industrially advantageous preparation process.

We claim:

1. A process for preparing D-lysine, which comprises the steps of:

bringing racemic lysine into contact with a culture or a treated culture of a microorganism having an ability of asymmetrically degrading L-lysine in a reaction medium; and collecting and isolating the D-lysine from the reaction mixture.

2. The process according to claim 1, wherein the microorganism having an ability of asymmetrically degrading L-lysine is a microorganism belonging to Achromobacter, Escherichia, Pseudomonas, Comamonas, Agrobacterium, Proteus, Flavobacterium, Hafnia, Providencia, Yarrowia, Candida or Apiotrichum.

3. The process according to claim 1, wherein the microorganism having an ability of asymmetrically degrading L-lysine is at least one selected from the group consisting of *Achromobacter delmarvae* IAM 1457 (FERM BP-5290), *Escherichia coli* ATCC 11303, *Escherichia coli* ATCC 11105, *Pseudomonas aureofaciens* IAM 1001, *Pseudomonas fragi* IAM 1650, *Pseudomonas pavonacea* IAM 1155, *Pseudomonas sp.* ATCC 14676, *Pseudomonas putida* ATCC 12633, *Comamonas testosteroni* IAM 1048, *Agrobacterium tumefaciens* No. 417 (FERM BP-5291), *Proteus vulgaris* RIMD KS (IAM 120034), *Flavobacterium rigense* No. 35 (FERM BP-5289), *Hafnia alvei* IFO 3731, *Providencia rettgeri* IFO 13501, *Yarrowia lipolytica* IFO 0717, *Yarrowia lipolytica* IFO 1548, *Yarrowia lipolytica* IFO 0746, *Yarrowia lipolytica* IFO 1195, *Yarrowia lipolytica* IFO 1209, *Candida maltosa* IAM 12247 and *Apiotrichum humicola* ATCC 36992.

4. The process according to claim 1, wherein the microorganism having an ability of asymmetrically degrading L-lysine is a microorganism belonging to Pseudomonas, Comamonas or Yarrowia.

5. The process according to claim 1, wherein the microorganism having an ability of asymmetrically degrading L-lysine is a microorganism belonging to Pseudomonas

*aureofaciens, Pseudomonas fragi, Pseudomonas pavonacea, Pseudomonas putida, Comamonas testosteroni* or *Yarrowia lipolytica*.

6. The process according to claim 1, wherein the microorganisms having an ability of asymmetrically degrading L-lysine is a microorganism selected from the group consisting of *Pseudomonas aureofaciens* IAM 1001, *Pseudomonas fragi* IAM 1650, *Pseudomonas pavonacea* IAM 1155, Pseudomonas sp. ATCC 14676, *Pseudomonas putida* ATCC 12633, *Comamonas testosteroni* IAM 1048, *Yarrowia lipolytica* IFO 0717, *Yarrowia lipolytica* IFO 1548, *Yarrowia lipolytica* IFO 0746, *Yarrowia lipolytica* IFO 1195 and *Yarrowia lipolytica* IFO 1209.

7. The process according to claim 1, wherein the step of bringing racemic lysine into contact with a culture or a treated culture of a microorganism having an ability of asymmetrically degrading L-lysine is carried out in a medium containing racemic lysine concurrently with culturing the microorganism having ability of asymmetrically degrading L-lysine.

8. The process according to claim 1, wherein the culture of the microorganism is a culture solution or a living cell, and the treated culture of the microorganism is a washed cell, a dried cell, a culture supernatant, a ground cell, an autolysate of a cell, an extract of a cell, or a partially purified or purified enzyme.

9. The process according to claim 1, wherein bringing racemic lysine into contact with a culture or a treated culture of a microorganism having an ability of asymmetrically degrading L-lyine is carried out in an aqueous solution at 10° to 50° C. and at a pH of 5 to 10.

10. The process according to claim 1, wherein bringing racemic lysine into contact with a culture or a treated culture of a microorganism having an ability of asymmetrically degrading L-lysine is carried out in an aqueous solution at 25° to 40° C. and at a pH of 6 to 9.

11. The process according to claim 1, wherein the charged concentration of the racemic lysine is 0.05 to 20% by weight of racemic lysine per volume.

12. The process according to claim 1, wherein the charged concentration of the racemic lysine is 0.5 to 10% by weight of racemic lysine per volume.

* * * * *

UNITED STATES PATENT AND TRADEMARK OFFICE
CERTIFICATE OF CORRECTION

PATENT NO. :     5,723,321
DATED      :     March 03, 1998
INVENTOR(S):     Masakatsu FURUI et al.

It is certified that error appears in the above-identified patent and that said Letters Patent is hereby corrected as shown below:

Claim 3, Column 6, line 54, "120034" should read --12003--.

Claim 9, Column 8, Line 8, "L- lyine" should read --L-lysine--.

Signed and Sealed this

Twenty-second Day of June, 1999

Attest:

Q. TODD DICKINSON

Attesting Officer            Acting Commissioner of Patents and Trademarks